(12) United States Patent
Huang et al.

(10) Patent No.: US 6,387,079 B1
(45) Date of Patent: May 14, 2002

(54) SAFETY SYRINGE

(75) Inventors: Wu-Shun Huang, 7F, No. 295, Sec. 2, Ho-Ping E. Rd.; Chung-Jen Lee, both of Taipei (TW)

(73) Assignee: Wu-Shun Huang, Taipei (TW)

(*) Notice: Subject to any disclaimer, the term of this patent is extended or adjusted under 35 U.S.C. 154(b) by 0 days.

(21) Appl. No.: 09/604,167

(22) Filed: Jun. 27, 2000

(51) Int. Cl.$^7$ ................................................ A61M 5/32
(52) U.S. Cl. ........................ 604/195; 604/110; 604/198; 128/919
(58) Field of Search .................. 604/27, 36, 93.01, 604/181, 187, 192, 195, 198, 218, 110, 243; 128/919

(56) References Cited

U.S. PATENT DOCUMENTS

| | | | |
|---|---|---|---|
| 5,569,203 A | * | 10/1996 | Chen |
| 5,899,887 A | * | 5/1999 | Liu |
| 6,033,385 A | * | 3/2000 | Liu |

\* cited by examiner

*Primary Examiner*—Sharon Kennedy
*Assistant Examiner*—Catherine Serke
(74) *Attorney, Agent, or Firm*—Rosenberg, Klein & Lee (57) ABSTRACT

A safety syringe ensuring stable and airtight connection of a hub to a barrel of the syringe is provided. A rear portion of the hub is tightly fitted in a neck portion at a front end of the barrel, such that the hub is prevented from moving out of the barrel via the neck portion. A first airtight contact line is formed at joint of two shoulder portions separately formed on the hub and the neck portion, and a second airtight contact line is formed at a position within a contact surface between the hub and the neck portion, so that the hub is stably and air-tightly connected to the barrel. A plunger is disposed in the barrel to push medical liquid in the barrel into the hub and a cannula fixed to the hub for injection purpose. An engaging cone having a slit is forward projected from a front end of the plunger to engage into receiving holes formed on the hub when the plunger is fully push forward. Any residual medical liquid in the barrel between the plunger and the hub flows backward via the slit to eliminate internal pressure in the barrel and thereby enables smooth injection of medical liquid into a patient's body.

3 Claims, 7 Drawing Sheets

SAFETY SYRINGE

BACKGROUND OF THE INVENTION

In the medical practices of early days, a used syringe would be thoroughly sterilized for repeated use later. Any incomplete serialization would dangerously cause a second time infection of a patient and/or any other people. To avoid such second time infection, disposable syringes are largely produced. However, large amount of discarded disposable syringes also bring us new problems of environmental pollution and safety of syringes in use. This is because no specific measures have been taken in disposing cannulas of the discarded syringes and exposed cannulas tend to easily stab nursing or cleaning personnel and result in even more infected people. To prevent discarded syringes and/or cannulas from unexpectedly stabbing and therefore undesirably injuring and infecting other people, including nursing and cleaning persons, various types of safety syringes are particularly developed, such as those disclosed in U.S. Pat. Nos. 5,562,627; 5,405,327; 5,569,203; 5,899,887; 5,395,346, etc. All of these previously disclosed syringes have specially associated hubs and barrels, so that hubs and cannulas held thereto of used syringes can be pulled back into the barrels without the risk of unexpectedly stabbing other people.

However, all these safety syringes of prior art having retractable hub and cannula developed to improve conventional syringes have a common issue, that is, the hubs of these safety syringes must be able to be stably connected to the barrels and be pulled back into the latter after the syringes have been used, while the hubs must be connected to the barrels in an absolutely airtight manner that is very important factor in providing good quality safety syringes.

As it is known that, when the hub is tightly connected to the barrel to ensure a good airtightness at the joint of these two members, it would be difficult to pull the hub back into the barrel easily; and when the easiness of pulling the hub back into the barrel is considered, it would be inevitable to sacrifice the airtightness between the hub and the barrel.

In the conventional retractable safety syringe, the hub and the used cannula are pulled back into the barrel by engaging a forward projected conic member on the plunger with holes provided on the hub. However, experiences in using such conventional retractable safety syringe indicate that an airtight small space is formed between the hub and the plunger when the latter is about to be fully pushed into the barrel to contact with the hub. At this point, any residual medical liquid in the hub would form a resistance to the tight engagement of the hub with the engaging conic member on the plunger. A nursing personnel needs to apply an increased force to push the plunger forward to ensure the full engagement of the conic member with the hub. Such increased force would cause a vibrating syringe and discomfort the patient.

It is therefore tried by the inventor to develop an improved safety syringe to eliminate the drawbacks existing in the conventional retractable safety syringe.

SUMMARY OF THE INVENTION

A primary object of the present invention is to provide an improved safety syringe, a barrel of which has a first shoulder provided in a neck portion thereof and a hub of which has a second shoulder provided around a middle portion thereof, such that the hub is retained to the neck portion by engagement of the first and the second shoulders with each other when the hub is pushed backward into the neck portion, and that an airtight contact line is formed at joint of the two shoulders to ensure airtight connection of the hub to the barrel.

Another object of the present invention is to provide an improved safety syringe, of which the neck portion of the barrel has an inner peripheral wall gradually diametrically reduced backward and the hub has an outer peripheral wall gradually diametrically reduced backward, and the hub has an outer diameter slightly larger than an inner diameter of the neck portion of the barrel, such that the hub is stably received in the neck portion in the manner of tight fit.

A further object of the present invention is to provide an improved safety syringe, of which the hub and the neck portion of the barrel is so designed in their diameters, lengths and inclinations that a second airtight contact line is formed at a certain position within the contact surface between the hub and the neck portion.

A still further object of the present invention is to provide an improved safety syringe, a plunger of which is provided at a front end with an engaging cone having a small slit. The engaging cone is adapted to engage into two receiving holes formed on the hub of the syringe when the syringe has been fully pushed forward in the barrel. The slit on the engaging cone allows residual medical liquid in the barrel between the plunger and the hub to flow backward into the barrel to enable smooth push of the plunger fully into the barrel.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
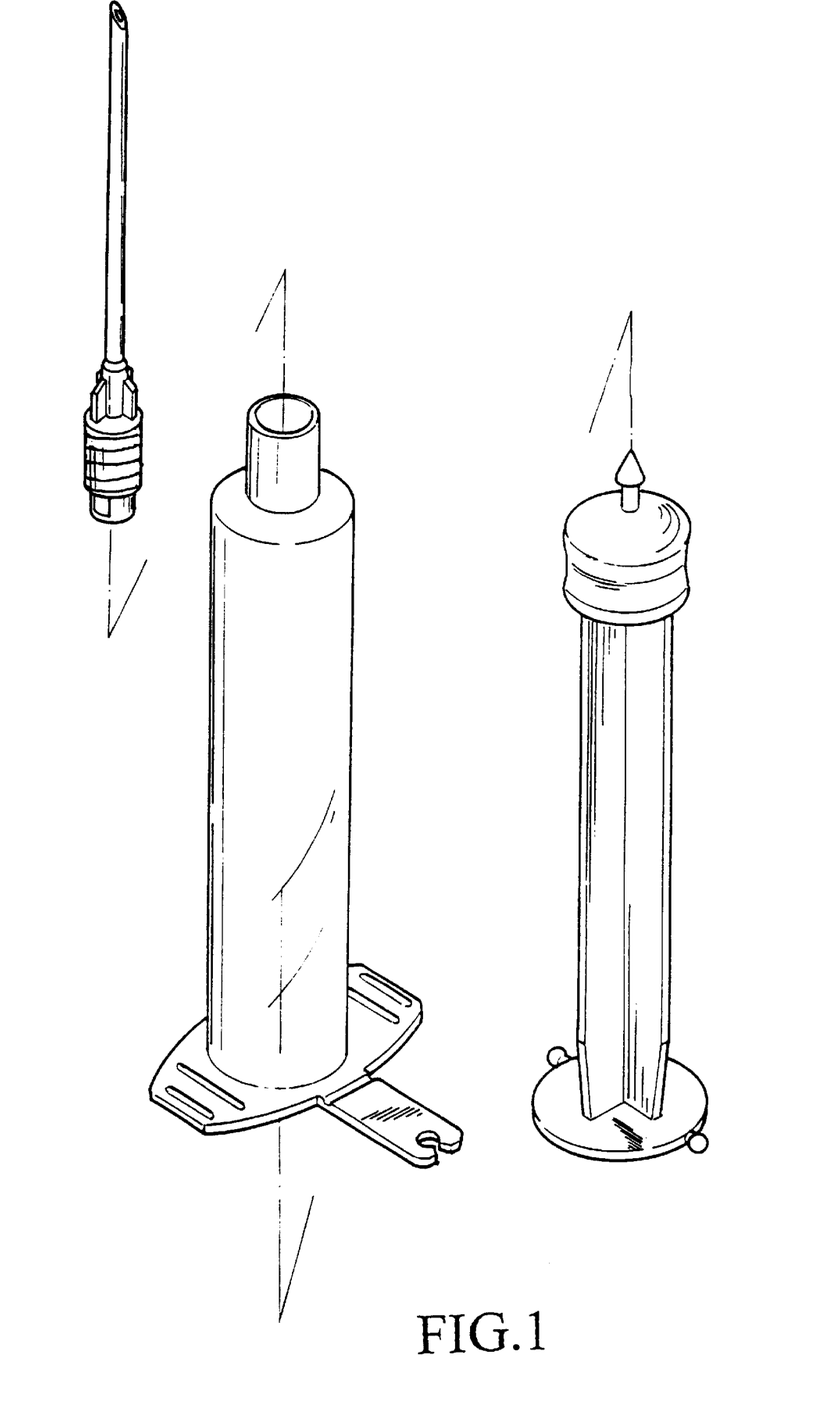
FIG. 1 is an exploded perspective of a conventional safety syringe.
Figure 2:
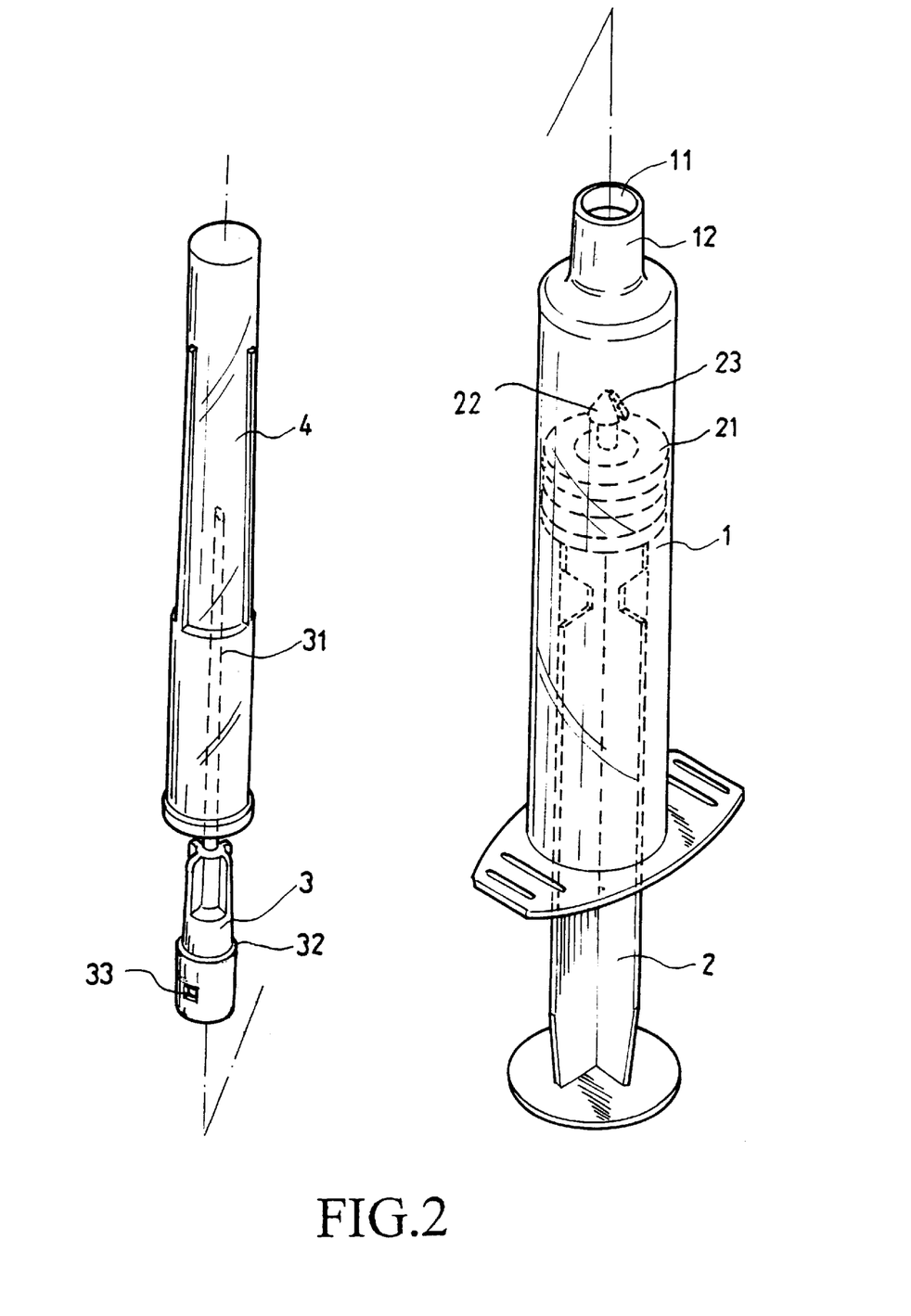
FIG. 2 is a partially exploded perspective of a safety syringe according to the present invention.

Please refer to FIG. 2 that is a partially exploded perspective of a safety syringe according to the present invention. The safety syringe of the present invention mainly includes a barrel 1, a plunger 2, a hub 3, and a cap 4.

The barrel 1 has a diameter-reduced neck portion that defines a front open end of the barrel 1. An inner peripheral wall 11 of the front open end of the neck portion inclines radially inward, so that a first shoulder portion 13 is formed between the inclined peripheral wall 11 and an inner peripheral wall 12 of the neck portion behind the inclined peripheral wall 11. The inner peripheral wall 12 of the neck portion is gradually diametrically reduced from an end having the first shoulder portion 13 toward a rear end of the neck portion.

The plunger 2 is extended into the barrel 1 via an opening provided at a rear end of the barrel 1. A stopper 21 is provided around a front end of the plunger 2 with an engaging cone 22 forward projected from a front end of the stopper 21. And, there is a small slit 23 radially extended from a point of the engaging cone 22 to a peripheral edge thereof.

The hub 3 has a cannula 31 fixed to a front end thereof, and is formed near and around a middle portion thereof with a second shoulder portion 32 and at a rear portion thereof with a radially extended channel which defines two diametrically opposite openings on the hub to serve as two receiving holes 33. An outer peripheral wall of a rear portion of the hub 3 behind the second shoulder portion 32 is gradually diametrically reduced toward a rear end of the hub 3.

The cap 4 is removably covered over the hub 3 and the cannula 31.

Figure 3:
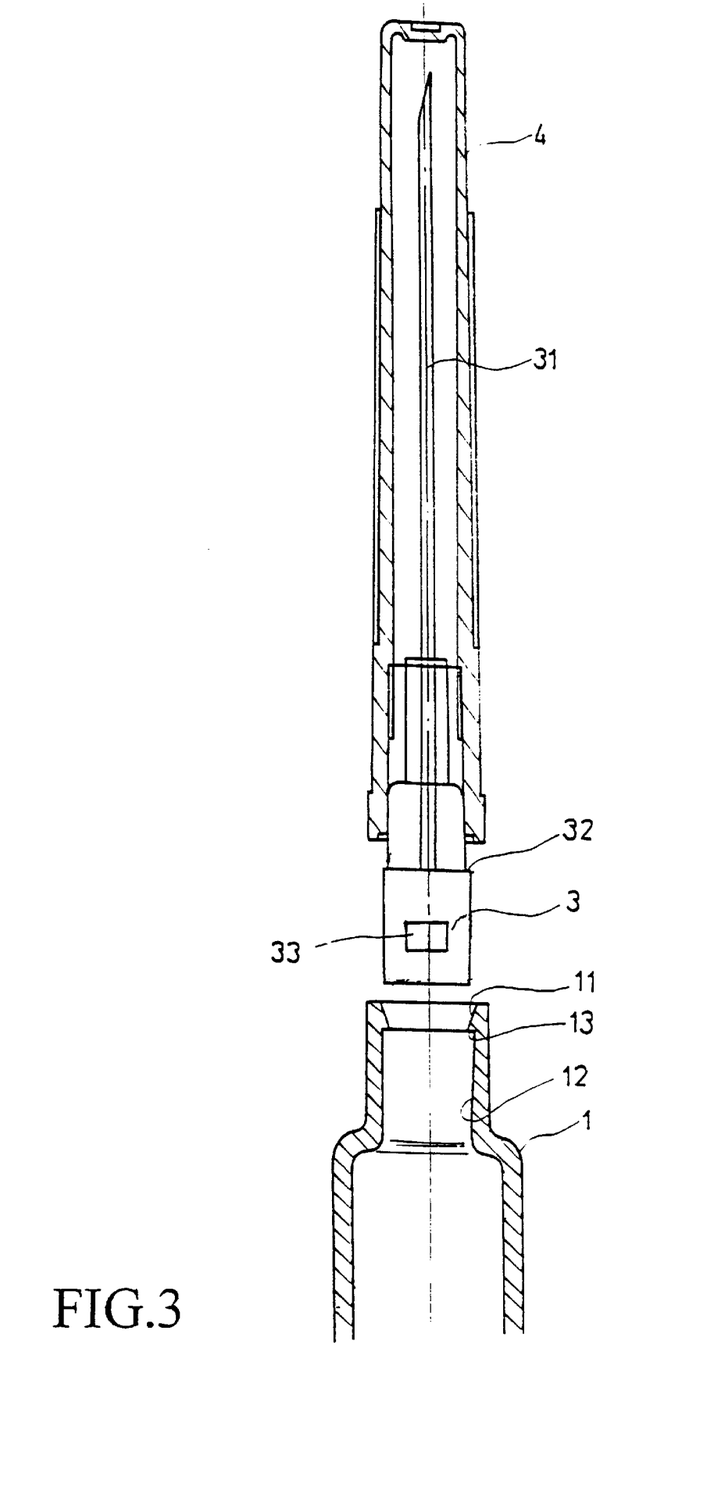
FIG. 3 is a fragmentary sectional view showing a hub of the safety syringe of FIG. 2 before being engaged into a barrel of the safety syringe of FIG. 2.
Figure 4:
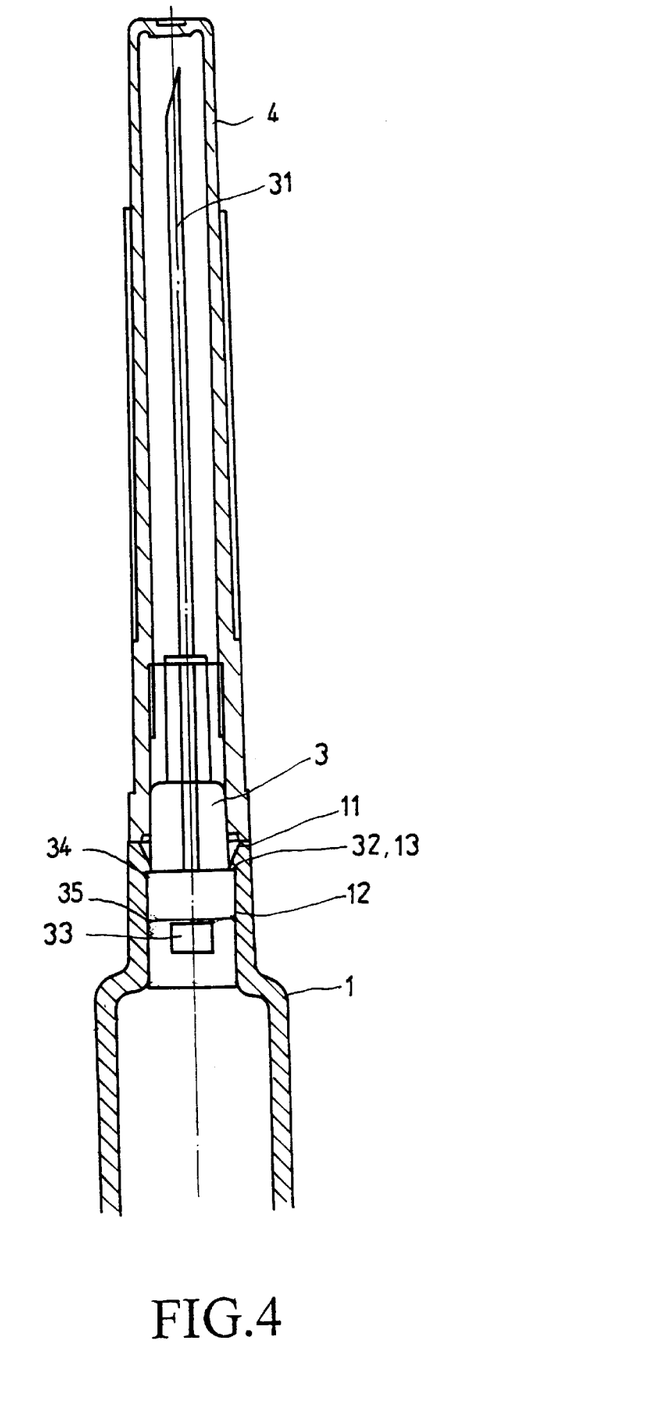
FIG. 4 is a fragmentary sectional view showing that the hub of FIG. 3 has been engaged into the barrel of the safety syringe of FIG. 2.

In assembling the safety syringe of the present invention, first extend the hub 3 and the cannula 31 fixed thereto into the cap 4. The cap 4 is so designed that it has an inner diameter similar to an outer diameter of a portion of the hub 3 above the second shoulder portion 32, so that the cap 4 is assembled to the front end of the hub 3 in the manner of tight fit, as shown in FIG. 3. Then, position the hub 3 into the barrel 1 by pushing the hub 3 rearward against the front open end of the neck portion until the second shoulder portion 32 of the hub 3 passes the radially inward inclined inner peripheral wall 11 and the first shoulder portion 13, as shown in FIG. 4. At this point, a first airtight contact line 34 is formed around a joint of the first and the second shoulder portions 13 and 32, and the hub 3 is tightly fixed in the neck portion of the barrel 1 and could no longer be moved out from the front open end of the neck portion. The gradually diametrically reduced outer peripheral wall of the rear portion of the hub 3 and the gradually diametrically reduced inner peripheral wall 12 of the neck portion of the barrel 1 are so designed in their diameters, lengths and inclinations that a second airtight contact line 35 is naturally formed around a certain position on a contact surface between the hub 3 and the neck portion when the hub 3 is tightly received in the neck portion. These two airtight contact lines 34 and 35 together ensure perfectly stable and airtight connection of the hub 3 to the barrel 1.

Figure 5:
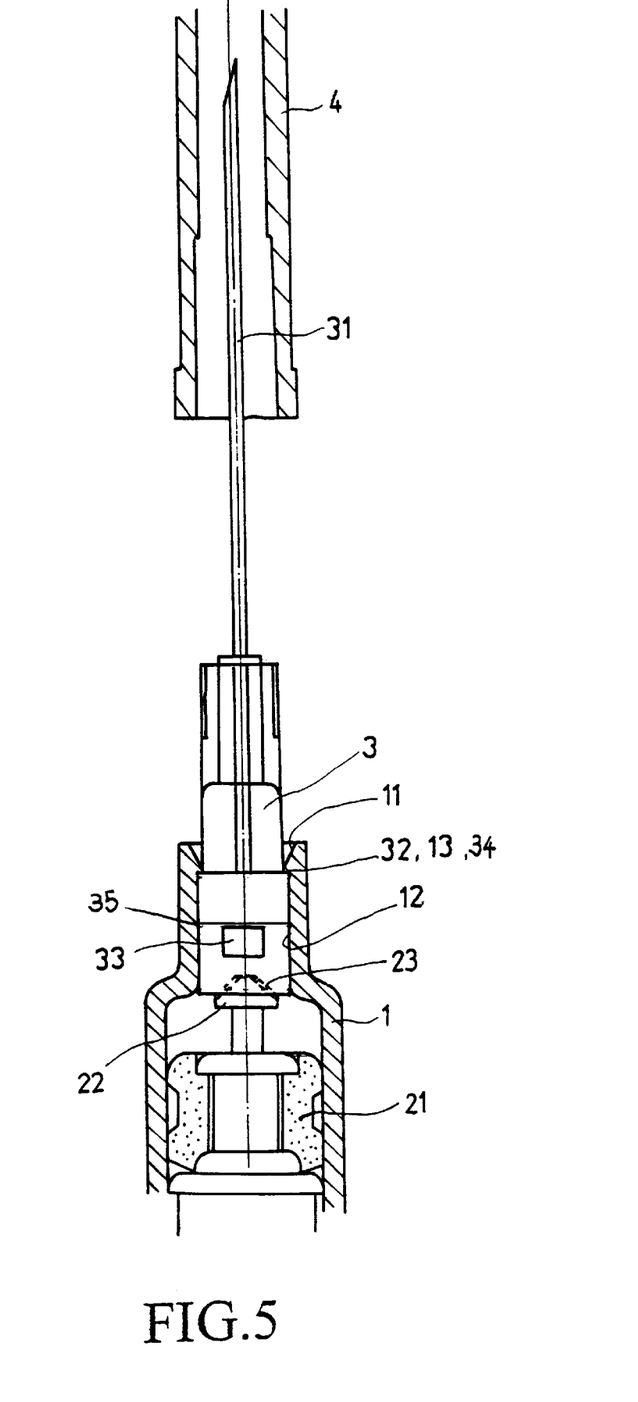
FIG. 5 is a fragmentary sectional view showing that a cap covering the hub is removed to expose a cannula mounted on the hub after the hub has been engaged into the barrel.
Figure 6:
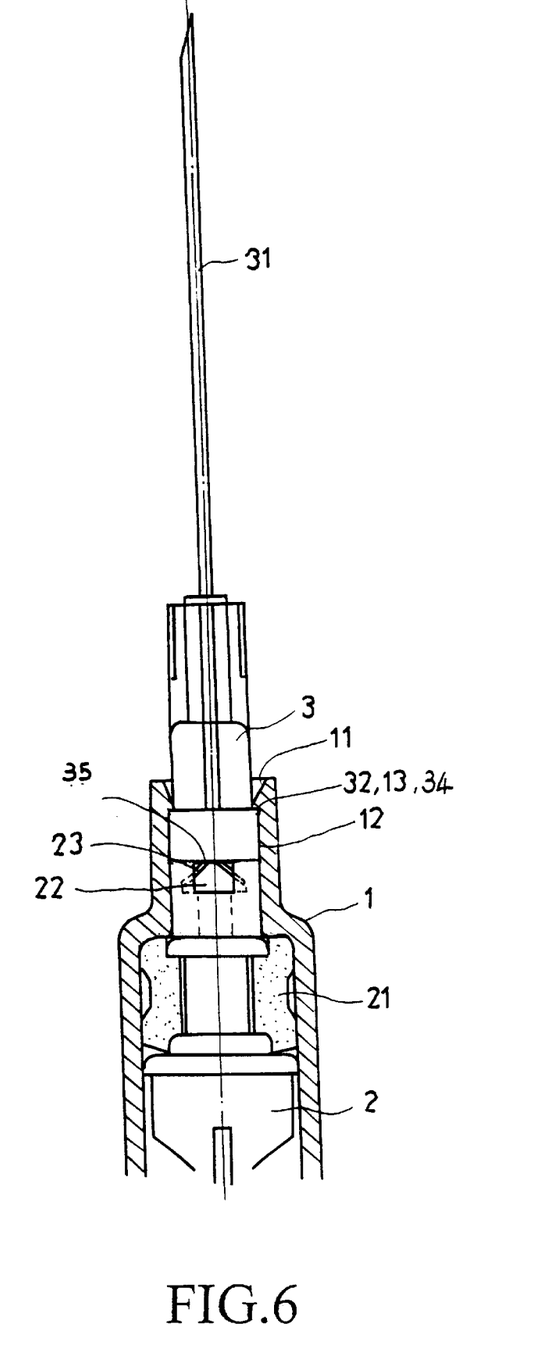
FIG. 6 is a fragmentary sectional view showing that a plunger of the safety syringe of FIG. 2 is fully pushed forward to engage a front end thereof with the hub.
Figure 7:
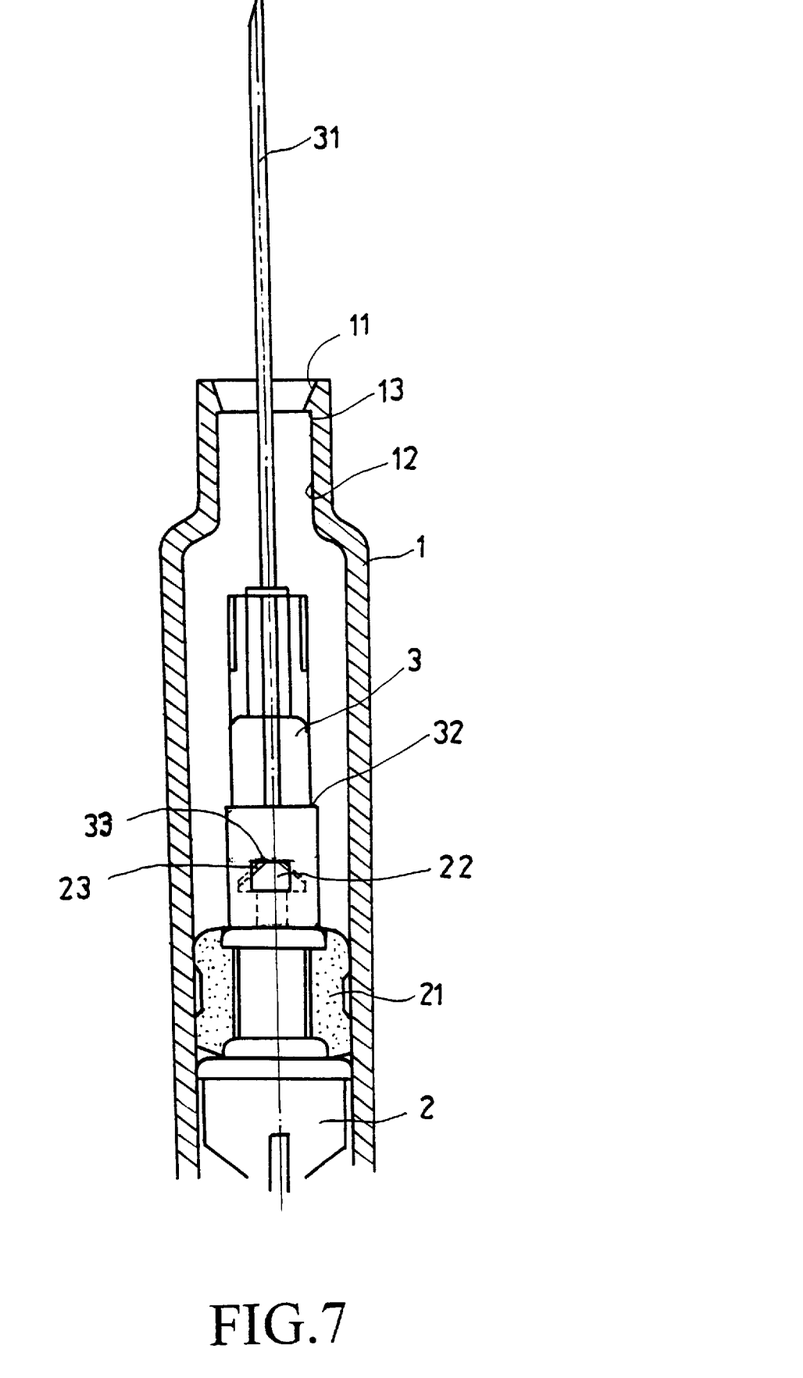
FIG. 7 is a fragmentary sectional view showing the hub and the cannula are pulled backward by the plunger into the barrel when the cannula has been used.

Finally, pull the cap 4 forward to expose the cannula 31 as shown in FIG. 5 and the safety syringe of the present invention is ready for injection. When the plunger 2 is pushed forward in the barrel 1 for the purpose of injection medical liquid and the engaging cone 22 at the front end of the stopper 21 on the plunger 2 is about to engage into the receiving holes 33 on the hub 3, any residual medical liquid in the barrel 1 is compressed by further movement of the plunger 2 toward the hub 3 and is brought to partially flow backward into the slit 23 radially provided on the bevel head of the engaging cone 22, allowing the plunger 2 to be further and smoothly pushed forward into the hub 3 without being stopped by an internal pressure between the stopper 21 of the plunger 2 and the hub 3, as shown in FIG. 6. With the slit 23, the problem of an overly strong push of the plunger 2 that would cause discomfort of patient being injected and an undesirable jetted medical liquid from the cannula 31 could therefore be avoided. After the injection, the plunger 2 is pulled backward to bring the hub 3 engaged with the engaging cone 22 of the plunger 2 and the used cannula 31 fixed to the hub 3 to move backward out of the neck portion and into the barrel 1, as shown in FIG. 7.

With the above arrangements, the safety syringe of the present invention in a fully assembled state is provided with two airtight contact lines 34 and 35 between the hub 3 and the barrel 1 to ensure firm, stable and airtight connection of the hub 3 and the cannula 31 to the barrel 1 and to eliminate drawbacks existing in the conventional retractable safety syringes. The safety syringe of the present invention is therefore novel, improved and practical for use.

What is claimed is:

1. A safety syringe, comprising a barrel, a hub, a cap and a plunger;

said barrel including a diameter-reduced neck portion extending to an open front end portion, said open front end portion having a radially inwardly inclining inner peripheral wall forming a first shoulder portion between said inner peripheral wall of said open front end portion and an inner peripheral wall of said neck portion, said inner peripheral wall of said neck portion being gradually diametrically reduced from said first shoulder portion to a rear end of said neck portion;

said hub having (a) a cannula fixed to a front end thereof, (b) a second shoulder portion circumscribing a middle portion of said hub, and (c) a radially extending channel formed adjacent a rear end of said hub and defining a pair of diametrically opposed openings therein to serve as receiving holes, an outer peripheral wall portion having a gradually reduced diameter between said second shoulder portion and said rear end of said hub;

said cap removably covering said cannula and a portion of said hub; and, said plunger being removably disposed in said barrel for injecting a medical liquid from within said barrel into a patient's body through said cannula, said plunger being an elongated member inserted into said barrel via an opening provided at a rear end of said barrel, said plunger having a stopper provided around a front end thereof with an engaging cone projecting forward from a front end of said stopper, said engaging cone being formed with a small slit extending radially from a pointed end of said engaging cone to a peripheral edge thereof, whereby when said hub is assembled into said neck portion of said barrel, said first and second shoulder portions are disposed in contact with each other to (a) provide a first airtight contacting surface joint therebetween, and (b) prevent said hub from moving out of said neck portion of said barrel, and said outer peripheral wall portion of said hub engaging said inner peripheral wall of said neck portion in substantially conformed manner to form a second airtight contacting surface joint therebetween.

2. A safety syringe comprising:

a barrel including a diameter-reduced neck portion extending axially therefrom, said neck portion having terminating at an open front end portion, said open front end portion defining an inclined first inner peripheral wall extending axially rearward and radially inward to form a first shoulder portion, said neck portion defining a second inner peripheral wall extending from said first shoulder portion in gradually diametrically reduced manner to a rear end thereof;

a hub coaxially coupled to said barrel having a cannula fixed to a front end thereof, said hub having an intermediate portion extending axially from said front end to a rear end, said hub including a second shoulder portion circumscribing said intermediate portion for engaging said first shoulder portion of said barrel, said intermediate portion having formed therein adjacent said rear end a pair of diametrically opposed receiving hole openings, said intermediate portion defining an outer peripheral wall portion frictionally engaging said second inner peripheral wall of said barrel neck portion in substantially flush manner, said outer peripheral wall portion being gradually reduced in diameter between said second shoulder portion and said rear end;

a cap removably covering said cannula and at least a portion of said hub; and, a plunger removably disposed in said barrel for injecting a medical liquid from within said barrel into a patient's body through said cannula, said plunger being an elongated member inserted into said barrel via an opening provided at a rear end of said barrel, said plunger having a stopper disposed at a front end thereof and an engaging cone projecting axially from a front end of said stopper for engaging said receiving hole openings of said hub intermediate portion upon substantially full insert of said plunger into said barrel;

said first and second shoulder portions forming a first airtight contacting surface joint therebetween when said hub is assembled with said neck portion of said to prevent detachment of said hub from said barrel neck portion, and said outer peripheral wall portion of said hub forming a second airtight contacting surface joint against said inner peripheral wall of said barrel neck portion.

3. The safety syringe as recited in claim 2 wherein said engaging cone has formed to extend axially therethrough at least one exhaust opening, whereby pressure accumulation adjacent said engaging cone is prevented.

* * * * *